US008812239B2

(12) United States Patent
Greenbaum et al.

(10) Patent No.: US 8,812,239 B2
(45) Date of Patent: Aug. 19, 2014

(54) METHOD AND SYSTEM FOR REAL-TIME ANALYSIS OF BIOSENSOR DATA

(75) Inventors: Elias Greenbaum, Knoxville, TN (US); Miguel Rodriguez, Jr., Oakridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1246 days.

(21) Appl. No.: 11/302,844

(22) Filed: Dec. 14, 2005

(65) Prior Publication Data

US 2007/0136834 A1 Jun. 14, 2007

(51) Int. Cl.
*G01N 33/50* (2006.01)
*G01N 33/48* (2006.01)
*G06F 19/00* (2011.01)

(52) U.S. Cl.
CPC .................................... *G06F 19/00* (2013.01)
USPC .................................................... 702/19

(58) Field of Classification Search
None
See application file for complete search history.

(56) References Cited

U.S. PATENT DOCUMENTS

| | | | | |
|---|---|---|---|---|
| 5,073,950 | A * | 12/1991 | Colbert et al. | 382/115 |
| 5,313,264 | A | 5/1994 | Ivarsson et al. | |
| 6,121,053 | A | 9/2000 | Kolber et al. | |
| 6,486,588 | B2 | 11/2002 | Doron et al. | |
| 6,511,854 | B1 | 1/2003 | Asanov et al. | |
| 6,569,384 | B2 | 5/2003 | Greenbaum et al. | |
| 6,573,107 | B1 | 6/2003 | Bowen et al. | |
| 6,726,881 | B2 | 4/2004 | Shinoki et al. | |
| 2002/0102629 | A1 * | 8/2002 | Greenbaum et al. | 435/34 |
| 2005/0065755 | A1 | 3/2005 | McCarter et al. | |
| 2005/0187667 | A1 * | 8/2005 | Vredevoogd et al. | 701/1 |

OTHER PUBLICATIONS

Motulsky et al., Fitting curves to data using nonlinear regression: a practical and nonmathematical review, Federation of American Societies for Experimental Biology, vol. 1, No. 5, pp. 365-374.*

Mayer Phillipp, et al., "A Simple In Vitro Fluorescence Method for Biomass Measurments in Algal Growth Inhibition Tests" Water Research, vol. 31, No. 10, 1997, pp. 2525-2531.

Zhang et al. "Calorimetric biosensors with integrated microfluidic channels", 2004, Biosensors and Bioelectronics, 19:1733-1743.

Khraiche et al. "Acoustic sensors for monitoring neuronal adhesion in real-time", 2003, Proceedings of the 25th IEEE Annual International Conference, 3:2186-2188.

Sanders et al. "Stand-off tissue-based biosensors for the detection of chemical warfare agents using a photosynthetic fluorescence induction", Biosensors and Bioelectronics 16(7-8):439-446.

Oliveria et al. "Magnetic resonance as a technique to magnetic biosensors characterization in *Neocapritermes opacus* termites", J. Magnetism and Magnetic Maters., 294:e171-e174.

Huang et al. "Development of infrared optical sensor for selective detection of tryosine in biological fluids", 2005, Biosensors and Bioelectronics, 21:408-418.

Hogan et al. "Chronic toxicity of uranium to a tropical green alga (*Chlorella* sp.) in natural waters and the influence of dissolved organic carbon", 2005, Aquatic Toxicology, 7:343-353.

Florescu, et al. "Development and evaluation of electrochemical glucose enzyme biosensors based on carbon film electrodes", 2005, Talanta, 65:306-312.

Chemla et al. "Ultrasensitive magnetic biosensor for homogenous immunoassay", 2000, PNAS, 97(26):14268-14272.

Wang et al. "Acoustic immunosensor for real-time sensing of neurotransmitter GABA", 2003, Proceedings of the 25th IEEE Annual International Conference, 4:2998-3000.

Rodriguez et al. "Biosensors for rapid monitoring of primary-source drinking water using naturally occuring photosynthesis", 2002, Biosensors and Bioelectronics, 17:843-849.

Buetler, M. et al., "A fluorometric method for the differentiation of algal populations in vivo and in situ," Photosynthesis Research, vol. 72, 2002, pp. 39-53.

* cited by examiner

*Primary Examiner* — Jason Sims

(74) *Attorney, Agent, or Firm* — Brinks, Gilson & Lione

(57) ABSTRACT

A method of biosensor-based detection of toxins includes the steps of providing a fluid to be analyzed having a plurality of photosynthetic organisms therein, wherein chemical, biological or radiological agents alter a nominal photosynthetic activity of the photosynthetic organisms. At a first time a measured photosynthetic activity curve is obtained from the photosynthetic organisms. The measured curve is automatically compared to a reference photosynthetic activity curve to determine differences therebetween. The presence of the chemical, biological or radiological agents, or precursors thereof, are then identified if present in the fluid using the differences.

7 Claims, 12 Drawing Sheets

Primary Data

Normal

Toxin $$\begin{pmatrix} n_1 \\ n_2 \\ . \\ . \\ n_n \end{pmatrix} = \begin{pmatrix} t_{11} & 0 & 0 & 0 & 0 \\ 0 & t_{22} & 0 & 0 & 0 \\ 0 & 0 & . & 0 & 0 \\ 0 & 0 & 0 & . & 0 \\ 0 & 0 & 0 & 0 & t_{nn} \end{pmatrix} \begin{pmatrix} cb_1 \\ cb_2 \\ . \\ . \\ cb_n \end{pmatrix}$$

The linear transformation matrix restores the toxin vector to the natural background vector. The diagonal elements are unique to each poison.

FIG. 11

METHOD AND SYSTEM FOR REAL-TIME ANALYSIS OF BIOSENSOR DATA

STATEMENT REGARDING FEDERALLY SPONSORED RESEARCH OR DEVELOPMENT

The United States Government has rights in this invention pursuant to contract no. DEAC05-00OR22725 between the United States Department of Energy and UT-Battelle, LLC.

CROSS REFERENCE TO RELATED APPLICATIONS

N/A

FIELD OF THE INVENTION

The present invention relates to sensors for detecting chemical, biological and/or radiological contaminants, or their precursors, in water or air.

BACKGROUND OF THE INVENTION

It is known that naturally-occurring algae can be used as biosensors for primary-source drinking water protection. For example, U.S. Pat. No. 6,569,384 to Greenbaum et al. describes a method for monitoring the variable fluorescence of algae that live in primary-source waters. Greenbaum et al. discloses using altered patterns of the fluorescence induction as a method for detecting the presence of toxins. Until now, the method used for assessing the presence of a toxin is to use standard numerical parameters that are derived from only two (2) specific points of the variable fluorescence induction curve. Software for obtaining these parameters is generally provided by the instrument manufacturer.

FIG. 1 shows a typical variable fluorescence induction curve from naturally-occurring algae in untreated river water. It can be seen from FIG. 1 that fluorescence emission during light activation is a time-dependent process. In particular there is an initial fluorescence, $F_o$, and a maximum fluorescence $F_{max}$. As shown in FIG. 1, the photochemical efficiency, Y, is generally calculated from the initial and maximum fluorescence values. It is known that specific toxins that can harm humans will alter the photochemical efficiency, Y. It is this alteration that is used as the signature for the presence of toxins. See, e.g., Rodriguez, Jr., M., Sanders, C. A. Greenbaum, E. 2002. "Biosensors for rapid monitoring of primary-source drinking water using naturally occurring photosynthesis", *Biosensors and Bioelectronics,* 17(10):843-849.

Accordingly, only two points ($F_{max}$ and $F_o$) of the chlorophyll fluorescence induction data are actually utilized. As a result, the information derived generally lacks sensitivity and speed in detecting and identifying potentially toxic agents, thus rendering the procedure to have limited value. What is needed is a methodology to utilize a larger portion of the data generated to provide improved sensitivity and speed in detecting and identifying potentially toxic agents.

SUMMARY

A method of biosensor-based detection of toxins includes the steps of providing a fluid to be analyzed having a plurality of photosynthetic organisms therein, wherein chemical, biological or radiological agents alter a nominal photosynthetic activity of the photosynthetic organisms. At a first time a measured photosynthetic activity curve is obtained from the photosynthetic organisms. The measured curve is automatically compared to a reference photosynthetic activity curve to determine differences therebetween. The presence of the chemical, biological or radiological agents, or precursors thereof, are then identified if present in the fluid using the differences.

In contrast to conventional data analysis which applies analysis routines (e.g. regression analysis) to fit experimental data to theoretical (reference) data, the invention instead analyzes data by comparing a measured curve to a reference photosynthetic curve, the reference curve being based on measured data itself, which and is generally updated over time.

The automatically comparing step preferably comprises nonlinear least-squares differential displacement analysis. The least-squares differential analysis minimizes a least squares difference between the measured curve and the reference curve. In this embodiment, the automatically comparing step can further comprise constructing a measured transformation matrix from the measured curve and reference transformation matrix from the reference curve. The determining step can then comprise calculating a degree of departure between the measured transformation matrix and the reference transformation matrix. The method preferably further comprises the step of constructing a transformation matrix that maps the measured curve into the reference curve.

The method can further comprise the step of identifying a specific chemical, biological or radiological agent, or precursor thereof. The identifying step can comprise comparing diagonal matrix elements of the transformation matrix to a library of stored diagonal matrix elements, wherein the library of stored diagonal matrix elements corresponding to respective ones of said chemical, biological or radiological agents, or precursors thereof.

The method can further comprise the step of obtaining a measured photosynthetic activity curve at an earlier time relative to the first time, and using the measured photosynthetic activity curve at the earlier time as the reference photosynthetic activity curve.

In one embodiment, the photosynthetic activity comprises chlorophyll fluorescence induction. In this embodiment, the fluid is drawn from a source of primary-source drinking water.

A water or air quality analysis system comprises a photodetector for measuring photosynthetic activity of a plurality of photosynthetic organisms, wherein chemical, biological or radiological agents alter a nominal photosynthetic activity of said photosynthetic organisms, and an electronics package including a processor coupled to the photodetector for analyzing the photosynthetic activity to indicate a presence of the chemical, biological or radiological agents in the water or air. The analyzing comprises obtaining at a first time a measured photosynthetic activity curve for the photosynthetic organisms, and comparing the measured curve to a reference photosynthetic activity curve to determine differences therebetween. The system can further comprise structure for communicating the measured photosynthetic activity or the measured photosynthetic activity after analysis by the electronics package to one or more remote sites.

BRIEF DESCRIPTION OF THE DRAWINGS

A fuller understanding of the present invention and the features and benefits thereof will be obtained upon review of the following detailed description together with the accompanying drawings, in which:

FIG. 5(*b*) shows a plot of sum of $R^2$ and the displacement when the control curve and test curve are not identical. A parabolic relationship still results. However, $R^2$ does not go to zero at any displacement.

FIG. 11 shows differential displacement analysis and diagonal matrix elements for characterizing the effect of toxins on variable fluorescence induction.

DETAILED DESCRIPTION

Figure 1:
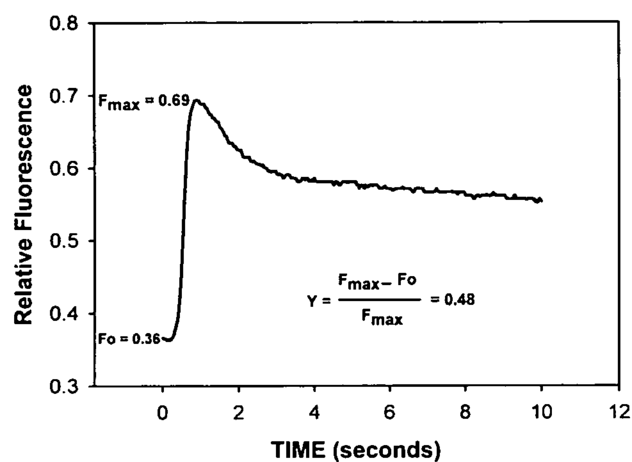
FIG. 1 shows a typical variable fluorescence induction curve provided by naturally-occurring algae.

A method of biosensor-based detection of toxins comprises the steps of providing a fluid to be analyzed having a plurality of photosynthetic organisms therein, wherein chemical, biological or radiological agents alter a nominal photosynthetic activity of the photosynthetic organisms. At a first time a measured photosynthetic activity curve is obtained from the photosynthetic organisms. The measured curve is automatically compared to a reference photosynthetic activity curve to determine differences therebetween, generally using an automated pattern recognition algorithm. The presence of the chemical, biological or radiological agents, or precursors thereof, are then identified if present in the fluid using the differences. As used herein, a "curve" corresponds an analog (continuous) sensor response function of a measured parameter (e.g. fluorescence), or more preferably digital data comprising at least two (2) points of data derived from digitizing the analog sensor response, where the at least two (2) points of data comprising the curve include data points other than $F_{max}$, $F_o$, Fs (steady state fluorescence), or data derived from these points (e.g. $Fv=F_{max}-F_o$; $RFd=F_{max}$ Fs). In a preferred embodiment, the "curve" corresponds to at least 10 points, and more preferably hundreds or thousands of data points obtained from the digitized analog sensor response.

The invention can also identify specific toxins. As described in detail below, a transformation matrix can be constructed that maps the measured curve into the reference (normal) curve. The diagonal matrix elements have been found to uniquely correspond to specific toxins. By comparing the obtained diagonal matrix elements to a library of predetermined diagonal matrix elements, specific toxins can be identified. If present, combinations of toxins which will generally produce a curve not found in a given library having curves of single toxins can also be determined using linear combination algorithms.

The invention is well suited for operation under real-world operating conditions of continuous water quality monitoring. The invention is also specifically tailored to use the data provided by fluorescence induction analysis to make a rapid objective assessment of the state of the photosynthetic organisms (e.g. algae or cyanobacteria) that are living in the water. Significantly, the invention quickly and efficiently can report the occurrence of a significant alteration in the expected shape of the variable fluorescence induction curve.

The gas or liquid medium to be monitored or analyzed is generally air in the case of gas and water in the case of liquid. The water can be primary-source drinking water. In a preferred embodiment of the invention, algae are the biosensors used to generate time-dependent biosensor signals such as fluorescence induction curves which permit classification of different toxic agents in surface source drinking water based on feature vectors. The inventors have previously demonstrated detection and identification of agents including methyl parathion (MPt), potassium cyanide (KCN), Diuron (DCMU), and Paraquat in both the samples of Clinch River (Oak Ridge, Tenn.) and the samples with lab-grown *Chlamydomonas reinhardtii* using photochemical efficiency (Y) calculated from the initial and maximum fluorescence values.

Biosensors are generally cell-based, and can include genetically modified cells. For example, a bacterium modified with lux genes can be used. This embodiment removes the need for an external light source. In the case of fluorescence induction, algae can be used, either naturally-occurring or genetically modified. Naturally-occurring aquatic algae do not generally require culturing.

Every natural water source that is exposed to sunlight contains populations of photosynthetic microorganisms (phytoplankton and algae, for example), at concentrations ranging from 10 to as high as 100,000 organisms/ml. Although always present in the water, these microorganisms are often invisible to the unaided eye. Phytoplankton emit a characteristic fluorescence signal that, if detectable in solutions with low microorganism concentrations, can be utilized as an in situ indicator of chemical and/or biological warfare agents that may have been added to water supplies. Biosensors provide time-dependent signals while in a gas or liquid medium to be monitored or analyzed for the presence of one or more toxins selected from chemical, biological or radiological agents. Water-soluble toxic chemical and/or biological agents, for example, can include blood agents (cyanide, for example), pesticides (methyl parathion, for example) and herbicides (DCMU, for example), or radionuclide that could pose a threat to primary-source drinking water supplies (e.g. uranium, see Alicia C. Hogan, Rick A. van Dam, Scott J. Markich and Caroline Camilleri "Chronic toxicity of uranium to a tropical green alga (*Chlorella* sp.) in natural waters and the influence of dissolved organic carbon", *Aquatic Toxicology,* 75(4):343-353, 2005).

The time-dependent biosensor signal is modified by the toxin as compared to a control signal when the toxin is absent. A variety of signal types can be analyzed using the invention. For example, the signals can be spectroscopic (e.g. fluorescence). Regarding spectroscopic signals, see, e.g., Huang, G. G., Yang, J. 2005 "Development of infrared optical sensor for selective detection of tyrosine in biological fluids", *Biosensors and Bioelectronics,* 21(3):408-418. Regarding acoustic signals, see, e.g., U.S. Pat. No. 6,486,588 to Doron, et al. "Acoustic biosensor for monitoring physiological conditions in a body implantation site"; "Acoustic immunosensor for real-time sensing of neurotransmitter GABA", *Proceedings of the 25th IEEE Annual International Conference,* 4:2998-3000.+Khraiche, M. L., Zhou, A., Muthuswamy, J. 2003, and "Acoustic sensors for monitoring neuronal adhesion in real-time", *Proceedings of the 25th IEEE Annual International Conference,* 3:2186-2188). Regarding electrochemical signals, see, e.g., U.S. Pat. No. 6,511,854 to Asanov, et al. "Regenerable biosensor using total internal reflection fluorescence with electrochemical control", and "Development and evaluation of electrochemical glucose enzyme biosensors based on carbon film electrodes" *Talanta,* 65(2):306-312.+Xu, J.-Z., et al. 2004.

Regarding thermal detection, see e.g., "Calorimetric biosensors with integrated microfluidic channels. *Biosensors and Bioelectronics",* 19(12):1733-1743.+Towe, B. C., Guilbeau, E. J. 1996. Regarding magnetic based sensors, see de Oliveira, J. F., et al. 2005 "Magnetic resonance as a technique to magnetic biosensors characterization in Neocapritermes opacus termites" *Journal of Magnetism and Magnetic Materials,* 292(2):e171-e174.+Chemla, Y. R., et al. 2000, "Ultrasensitive magnetic biosensor for homogeneous immunoassay", *Proc. Natl. Acad. Sci. USA,* 97(26): 14268-72. Regarding surface plasmon resonance (SPR) using enzymes or antibodies see, e.g., U.S. Pat. No. 6,726,881 to Shinoki, et al. "Measurement chip for surface resonance biosensor", U.S. Pat. No. 6,573,107 to Bowen, et al. "Immunochemical detection of an explosive substance in the gas phase through surface plasmon resonance spectroscopy", U.S. Pat. No. 5,313,264 to Ivarsson, et al. "Optical biosensor system".

In the case of air monitoring using algae-based biosensors, the algae generally requires culturing. In this embodiment, air to be analyzed can be drawn through filter paper having algae cultured thereon. See, e.g., Sanders, C. A., Rodriguez, Jr., M., Greenbaum, E. 2001. "Stand-off tissue-based biosensors for the detection of chemical warfare agents using photosynthetic fluorescent induction", *Biosensors and Bioelectronics,* 16(7-8):439-446.

Although the invention is generally hereafter described related to fluorescence induction provided by algal biosensors in water, as noted above, the invention is in no way limited to this specific embodiment. Embodied as a water quality sensor for drinking water, exemplary steps according to the invention may be summarized as follows:

1. Primary-source drinking water is monitored at regular intervals, for example every three to five minutes.
2. Each (analog) chlorophyll fluorescence induction curve that is acquired for each interval is digitized and stored. The shape of each curve is a recording of the physiological status of the algae at that point in time.
3. For each subsequent recording, such as three to five minutes later, the variable chlorophyll fluorescence induction curve at that time can be compared with the curve that was recorded three to five minutes earlier.
4. By using a nonlinear least-squares fit of the current data with the previous curve, a quantitative assessment can be made that determines the degree of departure of the current curve as compared to its predecessor.
5. Based on an algorithm, such as algorithms described herein, an objective real-time assessment of the degree of departure is obtained between the variable fluorescence curves and the correlation of that departure with the possible presence of toxins in the water.

Figure 2:
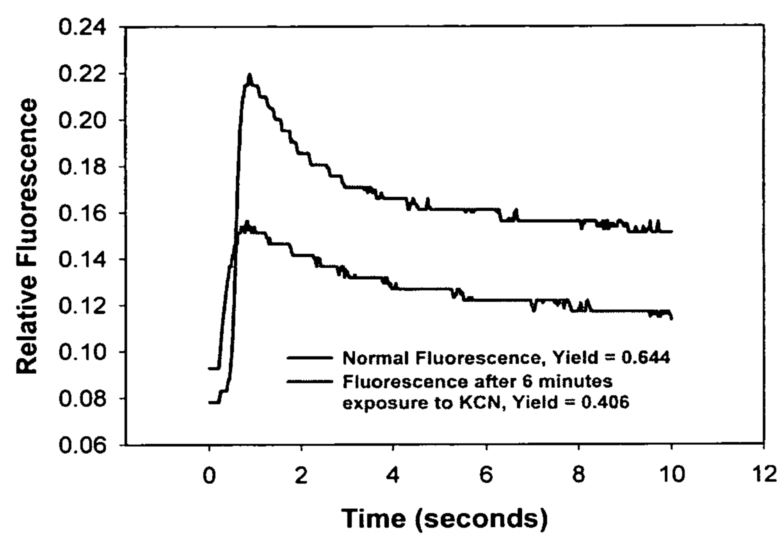
FIG. 2 illustrates a normal fluorescence induction curve and a fluorescence induction curve altered by the presence of the toxin potassium cyanide (KCN).

FIG. 2 illustrates a normal fluorescence induction curve and an altered fluorescence induction curve in the presence of potassium cyanide (KCN). Not only does the photochemical yield change, as expected, but the analytical shape of the curve is altered as well upon exposure to KCN. The present invention preferably establishes the degree of difference between the two curves based not only on numerical parameters that can be selected from the curves such as photochemical yield, but also based the extent to which the entire data set of the respective curves differ from each other based on differential displacement analysis to minimize the least squares difference between the curves and then constructing a transformation matrix to map the altered (poisoned) curve onto the control (non-poisoned) curve.

The least-squares minimization procedure is used to determine the relative position of sequential curves prior to constructing the transformation matrices. For most practical applications, each curve is evaluated in real-time as the reference for the subsequent curve, typically three to five minutes later. A transformation matrix is constructed for the two sequential curves that transforms or maps the subsequent curve back to the prior curve. The set of numbers, typically the diagonal elements of the matrix, contain all the information that is needed to reconstruct the prior curve from the data elements of the subsequent curve. Since it is known that the effect of toxins on variable fluorescence induction curves occurs on a timescale that is much quicker than the characteristic diurnal variations of physiological changes in the algae, this differential effect is used to make an objective determination regarding the presence of toxins in primary-source drinking water.

Data analysis typically comprises three steps. For example, first, a differential least-squares displacement analysis is performed to establish the preferred relative position between two sequential curves. Second, a linear transformation matrix is constructed whose diagonal elements contain the multiplicative coefficients that reconstruct the former curve from the latter curve (See FIG. 11). Third, the set of numbers that comprises the transformation coefficient is analyzed for specific patterns analyzed by custom software to detect "fingerprints" for specific toxins such as chemical toxins. Analysis of specific toxins is possible because, as the sample data provided herein shows, different poisons alter the natural fluorescence induction curve in different, specific ways. For example, a particularly simple case is one in which in which no poison has been added and there is no statistical difference between reference and measured (test) curves. In this ideal case, the parabola would also have a minimum of zero and the elements of the transformation matrix would all equal 1.

Figure 3:
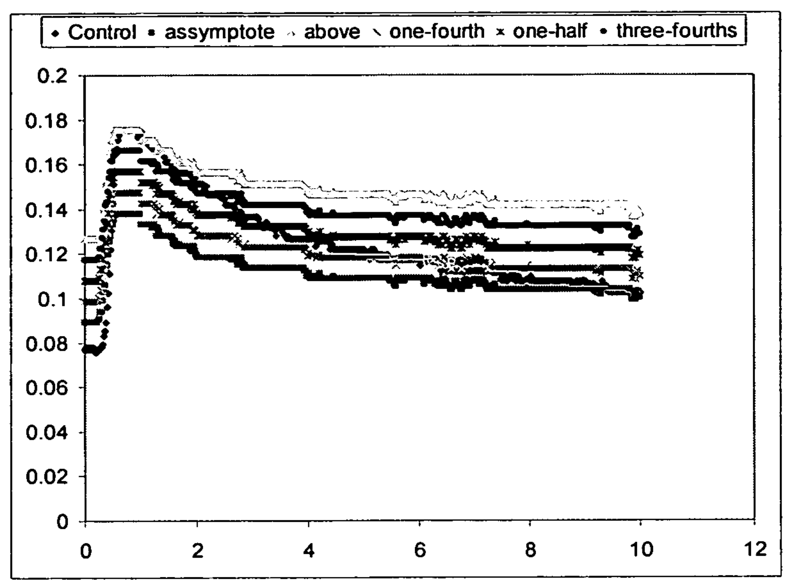
FIG. 3 shows a single control data curve (response without KCN toxin) plotted along with a response data curve (with KCN present) that is shown multiply plotted (5 times in this example) using various constant differential offset levels.

FIG. 3 shows control data (sensor response without KCN toxin) plotted along with response data (with KCN present) multiple times. The multiple plots are used to illustrate the relative positioning of the test data (using displacements) with the reference (control) data. Each KCN curve shown corresponds to a constant differential offset of the measured test data with respect to the reference (control). For each KCN curve, the summed square residuals $R^2$ are calculated to determine the relative position of the control and KCN curves that minimizes $R^2$. The transformation matrix is then constructed from these two curves to determine the diagonal matrix elements. It is this set of diagonal matrix elements that contains the set of information by which the normal fluorescence induction curve was altered by the KCN.

The range of displacement (offsets) of KCN data with respect to the control shown in FIG. 3 corresponds to a matching of the asymptotes (on the right hand side) near the 10-second mark. This corresponds to the lower KCN data curve. The upper range of displacement corresponds to a matching of the maximum fluorescence values for the control and KCN data. In this analysis, each KCN data point maintains its relative position with respect to each other data points in the same set, since the same constant differential (offset) is applied to each data value in a given data set. The range of differential offsets that are illustrated in FIG. 3 corresponds to a matching of asymptotes and peak fluorescence values as discussed above, plus additional offsets that correspond to selected positions of one fourth, one half, and three fourths between the lower and upper values. In practice, additional offsets can be applied to the test data to choose an adequate number of points for plotting $R^2$ versus differential displacement.

For the special case in which the reference and test data are identical, a plot of the sum of the square residuals $R^2$ versus displacement (offset) is parabolic in shape and has a zero minimum with respect to displacements above and below the control data set. This corresponds to the typical case when no toxins are introduced to the water in which the response of the biosensors is constant in time.

Figure 4:
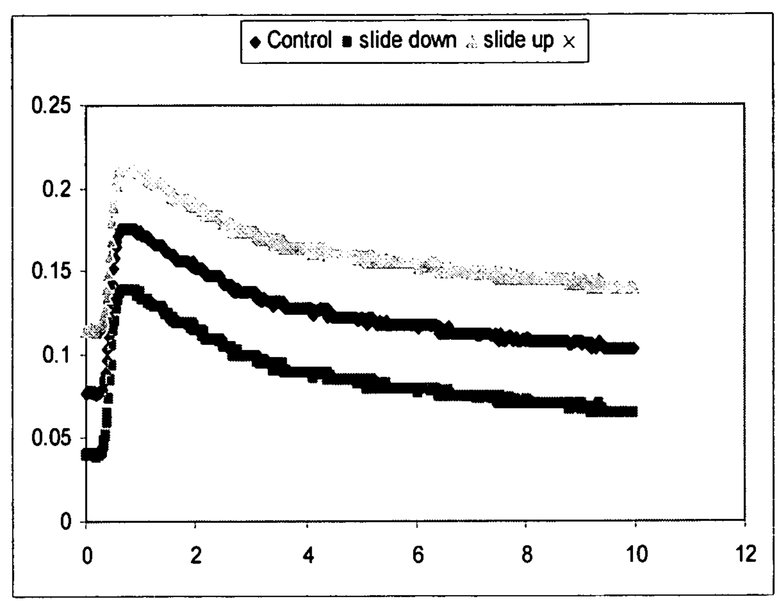
FIG. 4 shows a first KCN fluorescence data curve (center) as well as second and third KCN curves obtained from the first by adding (upper curve) or subtracting (lower curve) a constant differential offset to the original first center curve.

FIG. 4 shows KCN fluorescence data (center curve) as well as new curves obtained adding (upper curve) or subtracting (lower curve) a constant differential offset to the original (center) KCN data. If in this example the square residuals are computed as a function of displacement, the special case exists in which control and "test" are identical. Based on the analysis, a parabolic relationship is expected between $R^2$ and the displacement. $R^2$ goes to zero as the displacement goes to zero.

| Step | $R^2$ | |
|---|---|---|
| −0.5 | 0.68 | |
| −0.4 | 0.44 | |
| −0.3 | 0.25 | |
| −0.2 | 0.11 | |
| −0.1 | 0.03 | |
| 0 | 0.00 | ←Curves Coincide |
| 0.1 | 0.02 | |
| 0.2 | 0.10 | |
| 0.3 | 0.23 | |
| 0.4 | 0.42 | |
| 0.5 | 0.65 | |

Figure 5A:
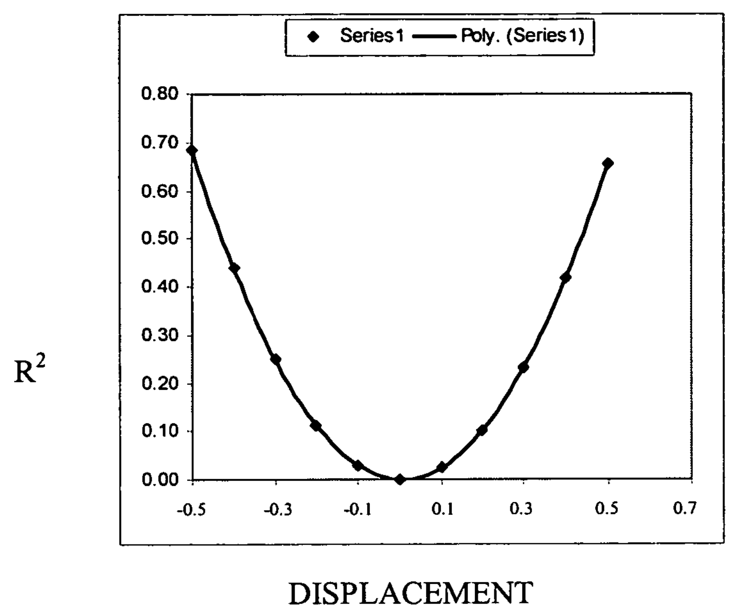
FIG. 5(*a*) shows a plot of sum of the residuals squares (($R^2$); y-axis) and the displacement (x-axis) when the control curve and test curve are identical. A parabolic relationship results and $R^2$ goes to zero at zero displacement.
Figure 5B:
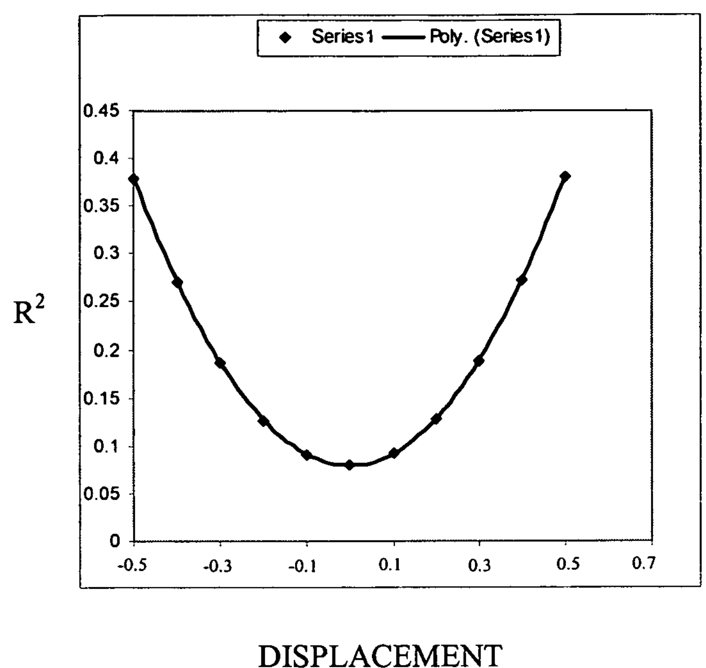

FIG. 5(*a*) shows a plot based on the TABLE data above of sum of the residuals squares (($R^2$); y-axis) and the displacement (x-axis) when the control curve and test curve are identical. A parabolic relationship results and $R^2$ goes to zero at zero displacement.

FIG. 5(*b*) shows a plot of sum of $R^2$ and the displacement when the control curve and test curve are not identical, such as obtained in the case of a toxin. A parabolic relationship still results. However, $R^2$ does not go to zero at any displacement. The smooth curves shown in FIGS. 5(*a*) and (*b*) were second-order polynomial fit using the trend line feature of the Microsoft Excel® program.

Figure 6:
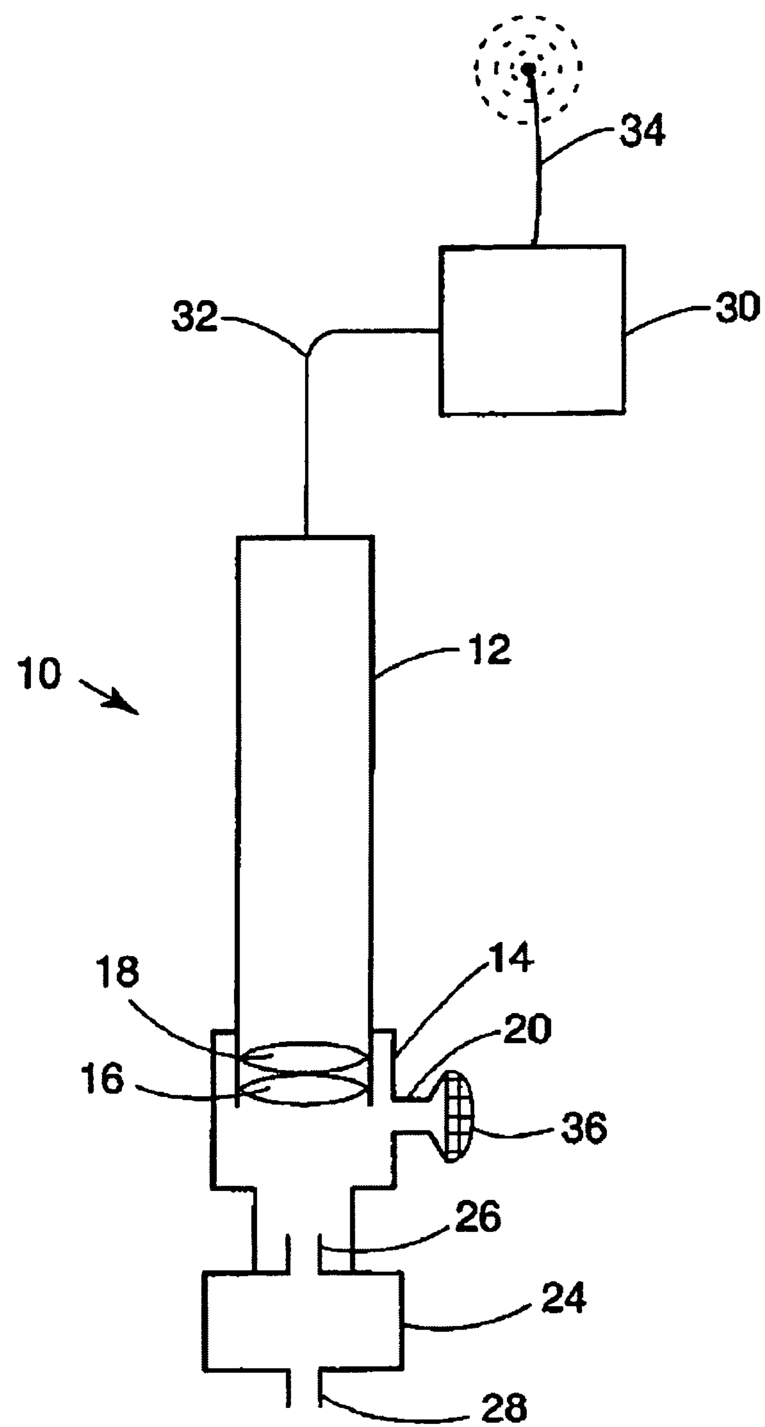
FIG. 6 is a schematic of an exemplary biosensor system for carrying out the method of present invention.

A variety of detection systems based on the invention can improve the sensitivity and speed in detecting and identifying potentially toxic agents. One embodiment is a robust field-deployable system. An automated biosensor system 10 for carrying out the method of present invention is shown schematically in FIG. 6. A photodetector 12, such as a luminometer or fluorometer, is attached to a cell 14 so that a cell window 16 faces the photodetector input 18. The cell has an inlet 20 having an optional particulate filter 36 and an outlet 26 for passing water therethrough. A pump 24 draws water from the outlet 26 and expels same through an exit 28. The cell 14 could have a displacement pump which draws water into the cell and expels same through a common inlet/outlet opening (analogous to 20), obviating outlet 26 and exit 28. Any means for introducing water into the cell and discharging water from the cell is suitable for carrying out the present invention.

The photodetector 12 must be of sufficient sensitivity for measuring photosynthetic activity of naturally-occurring, free-living, indigenous photosynthetic organisms drawn into the cell 14 with sample water. Applicants have used a Walz XE-PAM pulse-amplitude-modulation fluorometer available from Heinz Walz GmbH.Eichenring 6.D.91090 Effeltrich-.GERMANY.

The photodetector 12 is electrically connected by a connector 32 to an electronics package 30, which includes a power supply, systems for operating the photodetector 12 and pump 24, data processing electronics, and a transmitter that transmits a signal through an antenna 34. The electronics package 30 contains commonly used devices that are well known in the art. The particular components that are used therein, and the particular method of gathering and transmitting data are not critical to the operation of the present invention. The processor for analyzing data can be co-located with electronics package 30, or at a remote site having antenna 24.

Operation of the biosensor 10 can be constant sampling or intermittent sampling. Intermittent operation can be random sampling or timed sampling. The pump 24 is operated to cause water to flow through the cell 14. The photodetector 12 is activated to measure fluorescence in the water flowing through the cell 14. In a preferred embodiment, the electronics package 30 implements a processor running algorithms for analyzing raw data from the photodetector 12, and emits a signal through the antenna 34 indicating the presence and/or absence of chemical warfare agent(s) in the water, as well as the identity of the agent(s). The signal is received by equipment that indicates and/or records the data.

Although the invention is generally described for analyzing chlorophyll fluorescence induction curves, the invention has much broader applicability. Any 2D or 3D curve or surface that compares a first curve or surface with a second curve or surface can be characterized using the invention. For example, in addition to a time-dependent response, the response can be wavelength-dependent, such as absorption vs. wavelength spectroscopy data. In this embodiment, a transformation matrix that maps curve 2 onto curve 1 as a function of wavelength will contain a set of diagonal elements that fully characterizes the change between the two curves. This set of numbers contains information that can be used to identify the cause of the change.

Examples

It should be understood that the Examples described below are provided for illustrative purposes only and do not in any way define the scope of the invention.

FIG. 2 shows analyzed data from Clinch River water sample following a 10-minute exposure to KCN. FIG. 5(*b*) illustrates least-squares ($R^2$) minimization by progressively displacing the KCN data with respect to the control data and at each step of differential displacement calculating $R^2$. In FIG. 5(*a*) (no toxin), $R^2$ goes through zero whereas in FIG. 5(*b*) (toxin; KCN) $R^2$ does not go through zero. As noted above regarding FIG. 5(*a*), $R^2$ going through zero occurs when the two curves precisely overlapped. In that case, each data point is equal to the corresponding values of the other curve. The diagonal elements of the transformation matrix are all equal to 1. In FIG. 5(*b*) on the other hand, although $R^2$ goes through a minimum, it is not zero because KCN dramatically alters the analytical shape of the resulting curve. No differential displacement for the KCN data exists that enables complete overlap of all the data points simultaneously. Therefore, even though a minimum for $R^2$ is achieved, that minimum will never be zero. The degree to which the minimum $R^2$ departs from zero is a measure of the magnitude effect caused by the toxin, in this case KCN. The minimum value is used to fix the relative positions of the two curves from which the transformation matrix will be constructed.

Figure 7:
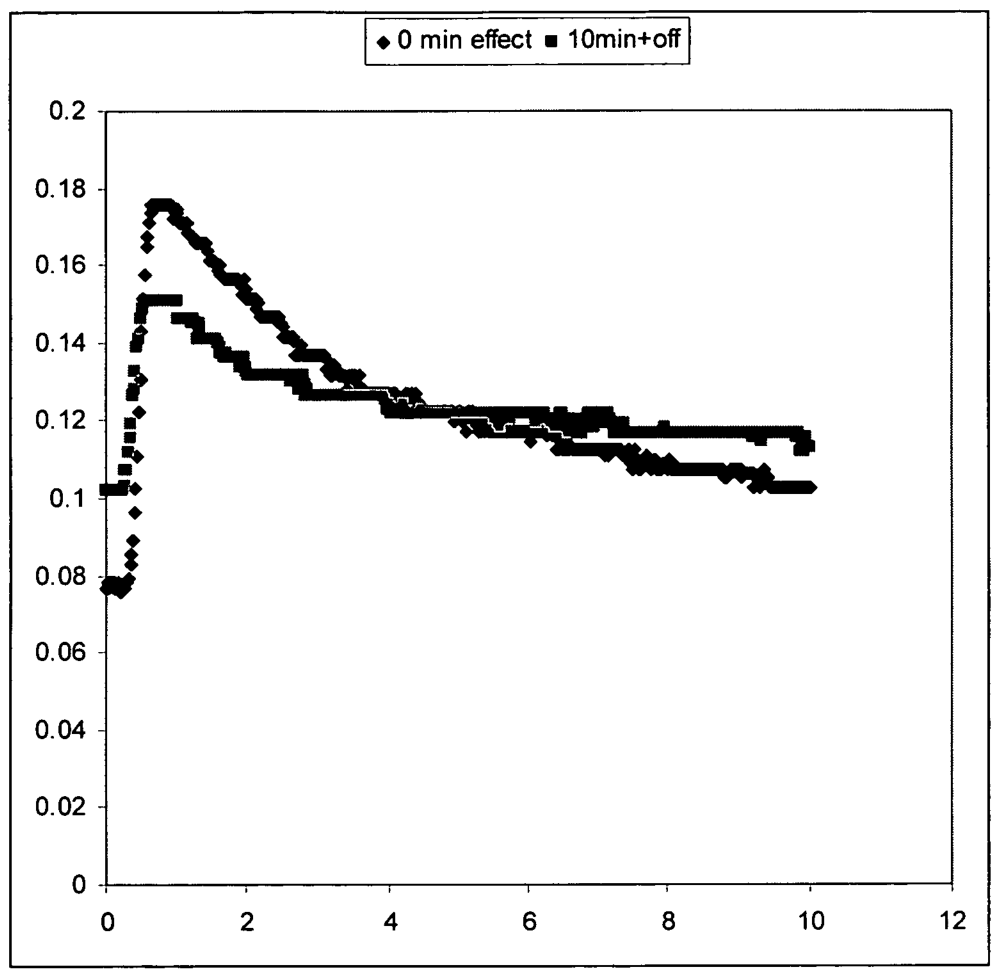
FIG. 7 shows biosensor data from a sample of Clinch River water following a 10-minute exposure to KCN. The Clinch River is the main source of drinking water supply for the city of Oak Ridge, Tenn.

Further inspection of FIG. 7 provides additional information regarding advantages of using this embodiment of the invention for data analysis. The displacement position selected for the KCN data of this Fig. corresponds to the approximate minimum of $R^2$. FIG. 7 shows that there is a balanced distribution of the control data points above and below those of the KCN values. The areas and geometric shapes defined by these two data sets have been found to be unique for the specific toxin that is detected. Thus, this method of bias sensing and toxin detection can be used to transform chemical identity into a geometric pattern. Accordingly, the invention can be used to not only detect the presence of toxins but also to identify them by using principles of analytic geometry, pattern recognition, and image transformations based on the geometry of the intersecting curves.

Figure 8:
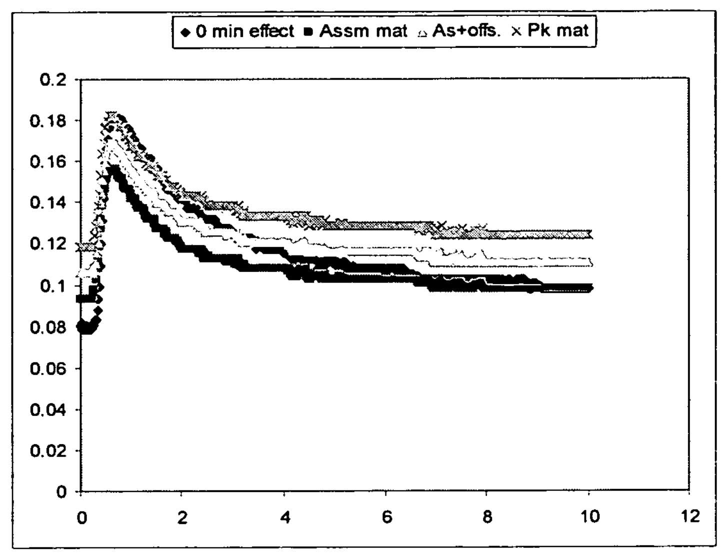
FIG. 8 shows the effect of 10-minute exposure to methyl parathion. The control is shown at zero minutes. Three levels of displacement are also shown.
Figure 9:
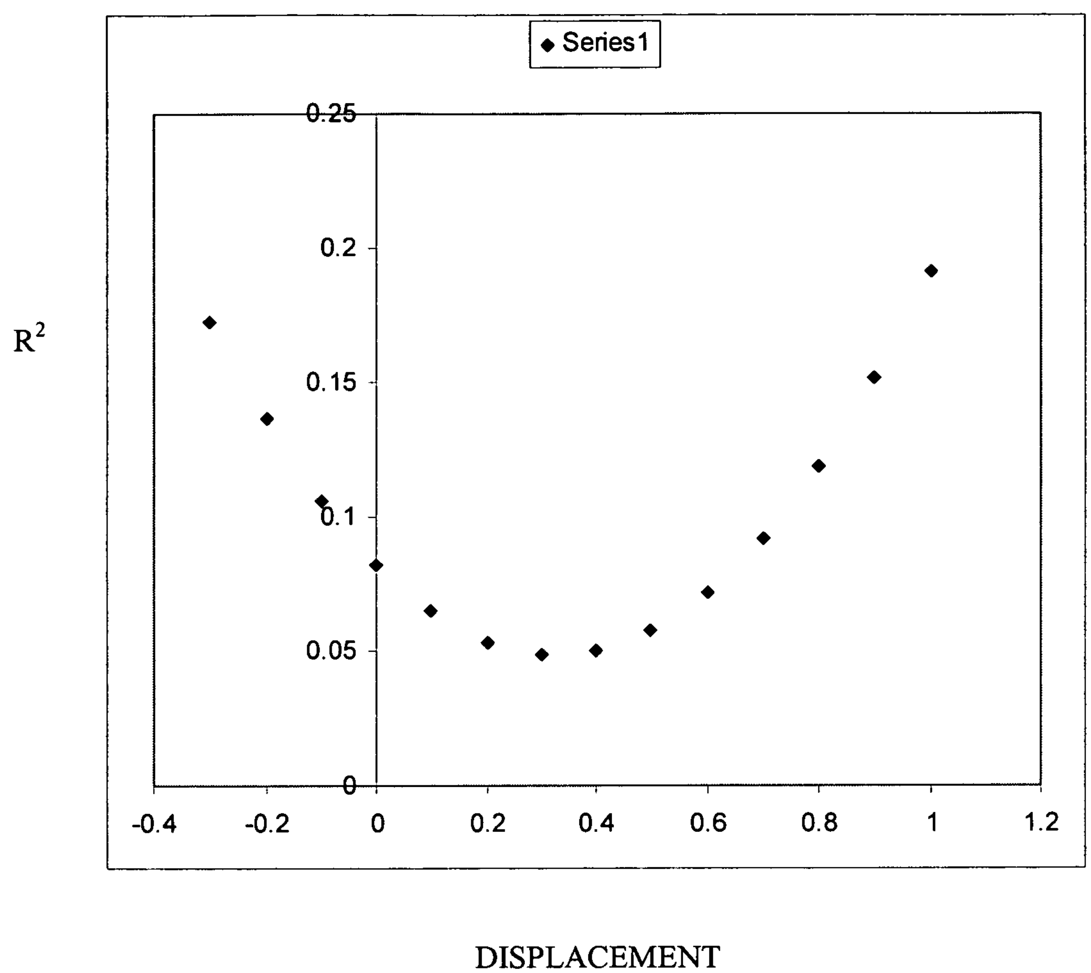
FIG. 9 shows values of $R^2$ as a function of differential displacement of the methyl parathion data with respect to control data.

FIG. 8 shows methyl parathion test data along with control data. The data of FIG. 8 represents the control and test data following a 10-minute exposure to methyl parathion. Three displacement levels have been chosen for the positions for the methyl parathion data. The lower curve corresponds to matching between control and methyl parathion at the asymptotic level on the right (at about t=10 seconds). The upper curve matches the peak values and the yellow curve is place midway between these two. The plot of $R^2$ versus displacement is illustrated in FIG. 9. As can be seen in FIG. 9, the progressive values of $R^2$ pass-through a minimum. But since the effect of the methyl parathion is to change the shape of the variable fluorescence induction curve, at no point do the two curves overlap simultaneously. Therefore, $R^2$ never reaches zero (minimum value about 0.05).

Figure 10:
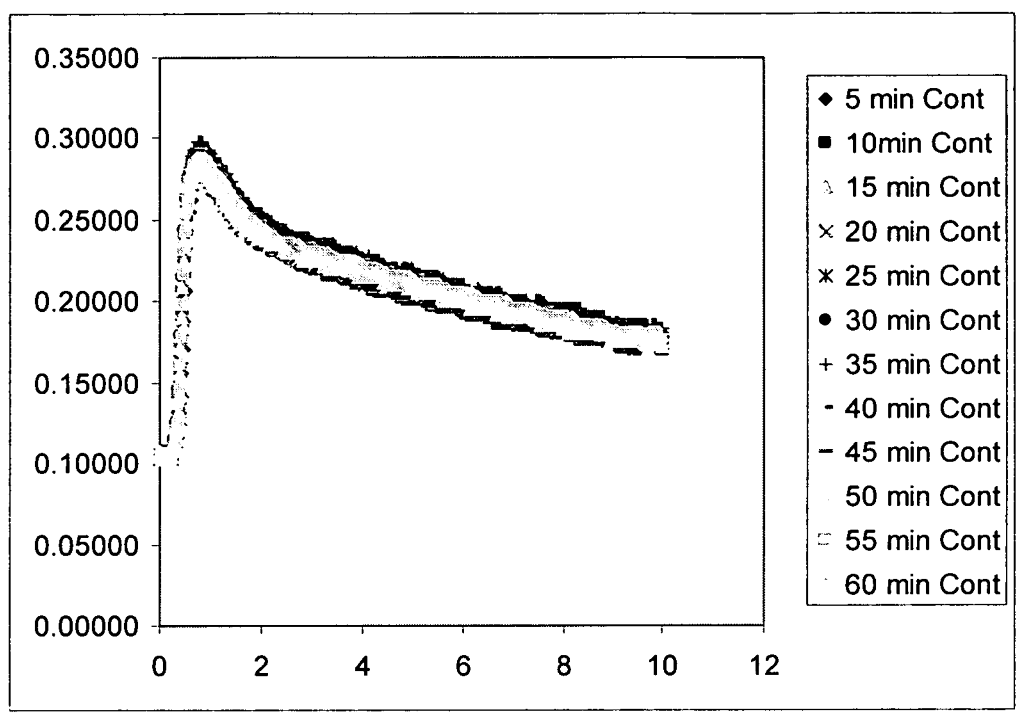
FIG. 10 shows twelve control experiments taken at five-minute intervals. A high degree of overlap between sequential fluorescence induction curves is demonstrated.

FIG. 10 further illustrates the principal of analysis with a series of control measurements associated with the methyl parathion experiments. A high degree of overlap for the sequence of 12 variable fluorescence induction curves taking at five-minute intervals is illustrated. Since all the curves virtually overlapped one another, $R^2$ will essentially equal zero for each of these curves when subject to the analysis as described above. Thus, for practical implementation of the invention, the signal that no poison is present yields a high degree of overlap, $R^2$ values that are close (or equal) to zero and diagonal matrix elements of the transformation matrix that are close to or equal to 1.

Linear mappings from one vector (normal background) to another vector (toxic background) thus can be used for rapid automatic detection and identification of toxins. FIG. 11 further illustrates this. The upper curve in the "primary data" and the "Normal" curve correspond to the response from healthy algae, whereas the lower curve in the "primary data" and the "Toxin" curve correspond to the response from algae following an exposure to a poison in primary-source drinking water from the Clinch River. The Toxin curve demonstrates transformation of the chlorophyll variable fluorescence induction curve.

The upper parabola corresponds to data for no toxin. In that case, the control and test data are the same and a differential displacement of the two curves results in an absolute minimum in which the summed square residuals ($R^2$) go to zero. This is illustrated by the minimum at zero for the "Normal" parabola. However, a simple visualization for the cyanide fluorescence induction curve in FIG. 11 indicates that the shapes of the two curves shown under "primary data" are fundamentally different. Accordingly, as shown by the Toxin parabola, the summed square residuals never go to zero although it can achieve a minimum as the cyanide curve is progressively displaced in the vertical direction and square residuals calculated for each displacement. The lower-left corner of the figure illustrates the transformation matrix whose diagonal elements uniquely characterize the effect of KCN on the fluorescence induction curve.

In a typical system according to the invention, the fluorescence data are digitized. A single fluorescence induction curve generally corresponds to approximately 1000 data points. Therefore, in such a case, each curve-control or toxin-corresponds to a single column vector of about 1000 elements. The vectors and transformation matrix correspond to the linear transformation of toxin vector to the normal or control vector. The transformation matrix, for minimum square toxin residuals, can be used to map each component of the toxin vector back to the normal vector. The coefficient of mapping for each component of the toxin vector is contained in the corresponding diagonal element of the transformation matrix. It is this ensemble of numbers comprising the diagonal elements of the transformation matrix ($t_{11}, t_{22} \ldots t_{nn}$) that contains the sum total information of how one vector maps into another.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A water or air quality analysis system, comprising:

a photodetector for measuring photosynthetic activity of photosynthetic organisms; and an electronics package comprising a processor coupled to the photodetector, the processor comprising executable instructions for analyzing qualitative changes in photosynthetic activity data that can indicate the identity of chemical, biological, or radiological agents;

where the executable instructions comprise:

obtaining a photosynthetic activity curve from the processor at a first time; and comparing at least two data points from the photosynthetic activity curve to at least two data points from a reference photosynthetic activity curve to identify the presence of a specific chemical, biological, or radiological agent;

and where the comparing comprises calculating a degree of difference between a first photosynthetic activity data point and a first reference photosynthetic activity data point, and between a second photosynthetic activity data point and a second reference photosynthetic activity data point;

the calculating comprises adding or subtracting a constant differential offset to at least the first and second photosynthetic activity data points to obtain at least first and second offset photosynthetic activity data points; and the comparing further comprises calculating at least a first transformation coefficient that maps the first offset photosynthetic activity data point to the first reference photosynthetic activity data point, and a second transformation coefficient that maps the second offset photosynthetic activity data point to the second reference photosynthetic activity data point.

2. A water or air quality analysis system, comprising:

a photodetector for measuring photosynthetic activity of photosynthetic organisms; and an electronics package comprising a processor coupled to the photodetector, the processor comprising executable instructions for analyzing qualitative changes in photosynthetic activity data that can indicate the identity of chemical, biological, or radiological agents;

where the executable instructions comprise:

obtaining a photosynthetic activity curve from the processor at a first time; and comparing at least two data points from the photosynthetic activity curve to at least two data points from a reference photosynthetic activity curve to identify the presence of a specific chemical, biological, or radiological agent;

and where the comparing comprises calculating a degree of difference between a first photosynthetic activity data point and a first reference photosynthetic activity data point, and between a second photosynthetic activity data point and a second reference photosynthetic activity data point;

the comparing comprises calculating, for each photosynthetic activity data point from the photosynthetic activity curve, a degree of difference between a photosynthetic activity data point and a reference photosynthetic activity data point;

the calculating comprises adding or subtracting a constant differential offset to each of the photosynthetic activity data points to obtain a plurality of offset photosynthetic activity data points;

the constant differential offset minimizes a sum of the square residuals between the photosynthetic activity data points and the reference photosynthetic activity data points; and the comparing further comprises calculating a plurality of transformation coefficients that map the offset photosynthetic activity data points to the photosynthetic activity data points.

3. The system of claim 2, where the executable instructions further comprise identifying the presence of one or more specific chemical, biological, or radiological agents by comparing the transformation coefficients to reference transformation coefficients corresponding to specific chemical, biological, or radiological agents.

4. A water or air quality analysis system, comprising:

a photodetector for measuring photosynthetic activity of photosynthetic organisms; and an electronics package comprising a processor coupled to the photodetector, the processor comprising executable instructions for analyzing qualitative changes in photosynthetic activity data that can indicate the identity of chemical, biological, or radiological agents;

where the executable instructions comprise:

obtaining a photosynthetic activity curve from the processor at a first time; and comparing at least two data points from the photosynthetic activity curve to at least two data points from a reference photosynthetic activity curve to identify the presence of a specific chemical, biological, or radiological agent;

and where:

the comparing comprises calculating a degree of difference between a first photosynthetic activity data point and a first reference photosynthetic activity data point, and between a second photosynthetic activity data point and a second reference photosynthetic activity data point; and the comparing further comprises calculating at least a first transformation coefficient that maps the first photosynthetic activity data point to the first reference photosynthetic activity data point, and a second transformation coefficient that maps the second photosynthetic activity data point to the second reference photosynthetic activity data point.

5. The system of claim 4, where the executable instructions further comprise identifying the presence of one or more specific chemical, biological, or radiological agents by comparing the transformation coefficients to reference transformation coefficients corresponding to specific chemical, biological, or radiological agents, or portions thereof.

6. A water or air quality analysis system, comprising:

a photodetector for measuring photosynthetic activity of photosynthetic organisms; and an electronics package comprising a processor coupled to the photodetector, the processor comprising executable instructions for analyzing qualitative changes in photosynthetic activity data that can indicate the identity of chemical, biological, or radiological agents;

where the executable instructions comprise:

obtaining a photosynthetic activity curve from the processor at a first time; and comparing at least two data points from the photosynthetic activity curve to at least two data points from a reference photosynthetic activity curve to identify the presence of a specific chemical, biological, or radiological agent;

and where:

the comparing comprises calculating a degree of difference between a first photosynthetic activity data point and a first reference photosynthetic activity data point, and between a second photosynthetic activity data point and a second reference photosynthetic activity data point; and the comparing further comprises constructing a transformation matrix that maps the photosynthetic activity data points to the reference photosynthetic activity data points.

7. The system of claim 6, where the executable instructions further comprise identifying the presence of one or more specific chemical, biological, or radiological agents by comparing the transformation matrix to a reference transformation matrix corresponding to specific chemical, biological, or radiological agents, or portions thereof.

* * * * *